US00PP13143P2

(12) United States Plant Patent
Michalik

(10) Patent No.: US PP13,143 P2
(45) Date of Patent: Oct. 29, 2002

(54) VARIETY OF ANGELONIA PLANT NAMED 'ANSTERN'

(75) Inventor: Andrea Michalik, Dresden (DE)

(73) Assignee: Elsner pac Jungpflanzen (DE)

( * ) Notice: Subject to any disclaimer, the term of this patent is extended or adjusted under 35 U.S.C. 154(b) by 0 days.

(21) Appl. No.: 09/733,159

(22) Filed: Dec. 8, 2000

(65) Prior Publication Data

US 2002/0073456 P1 Jun. 13, 2002

(51) Int. Cl.[7] ..... A01H 5/00
(52) U.S. Cl. ..... Plt./263
(58) Field of Search ..... Plt./263

(56) References Cited

PUBLICATIONS

UPOV–ROM GTITM Computer Database, 2001/04, GTI jouve Retrieval Software, citation for 'Anstern'.*

* cited by examiner

*Primary Examiner*—Bruce R. Campell
*Assistant Examiner*—Susan B. McCormick
(74) *Attorney, Agent, or Firm*—Webb Ziesenheim Logsdon Orkin & Hanson, P.C.

(57) ABSTRACT

A new and distinct angelonia plant with blue two-colored flowers above medium green foliage. The plant is suitable for pot planting or as a bedding plant.

1 Drawing Sheet

CLASSIFICATION

Angelonia hybrid.

VARIETAL DENOMINATION

'Anstern'.

BACKGROUND OF THE INVENTION

The present invention comprises a new and distinct cultivar of Angelonia known by the varietal name 'Anstern'. The new variety was discovered in 1999 in a selective breeding program in Dresden, Germany. The new variety is the result of a combination breeding of 50 seedlings having blue colored flowers. A mutation of seedling An 27 resulted in the new variety. The new variety exhibits the flower color of its heritage in the purple region of its bicolored flowers, but differs in its growth and flower shape. The new variety was first asexually reproduced by cuttings in Dresden, Germany. The new variety has been trial and field tested and has been found to retain its distinctive characteristics and remain true to type through successive propagations.

The new variety differs from the unpatented variety 'AngelMist Purple' as follows:

| | 'Anstern' | 'AngelMist Purple' |
|---|---|---|
| Flower color | Bicolored | Purple |
| Flower size | Medium | Small |
| Growth | Erect | Trailing |

DESCRIPTION OF THE DRAWINGS

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions carried out in Dresden, Germany. The color readings were taken on plants grown in pots outdoors in shadow during summer. Color references are primarily to The R.H.S. Colour Chart of The Royal Horticultural Society of London.

PLANT

Form: Erect.
Height media surface to top of foliage: 50–60 cm.
Height media surface to top of cluster: 50–60 cm.
Growth: 7–20 stems depending on age of the plant.
Strength: Does not require artificial support.
Time to initiate roots: 3 weeks.
Leaves:
- *Size.*—10–14 cm long; 1.5–2.0 cm wide.
- *Shape.*—Lanceolate overall; pointed apex; pointed base.
- *Margin.*—Toothed.
- *Texture.*—Smooth.
- *Color.*—138A upper side; 138B underside.
- *Ribs and veins.*—Venation: Net-shaped, not parallel. Color: 138C.

Petioles: Absent.
Stem/branches:
- *Color.*—Green Group 138A.
- *Internode length.*—Vegetative: 3–4 cm. Generative: 1–1.5 cm.

THE BUD

Shape when just showing color:
- *Overall.*—Racemose.
- *Individual bud.*—Spherical.

Color: Green Group 136B.
Size of individual bud when just showing color: 0.3 cm wide; 0.3 cm long.

INFLORESCENCE

Blooming habit: Single, groups of two flowers may be present at each node with group 5–6 cm across.

Flowers:

*Form.*—Zygomorph.

*Number of flowers per plant.*—70–100.

*Size.*—3.0–3.5 cm wide; 4.0–4.5 cm long; maximum 1 cm deep.

*Petals.*—Color: Upper surface: 86B shading to 155C at edges. Lower surface: 86B shading to 155C at edges. Size: 2.5 cm long; 2.7 cm wide. Number per flower: 5 Shape: Ondulated. Margin: Smooth.

*Texture and appearance.*—Velvety.

Petaloids: Absent.

Pedicel:

*Length.*—2.5–3 cm.

*Diameter.*—1 mm.

*Color.*—138B.

Disease/pest resistance: No unusual susceptibility to diseases or pests has been noted to date.

Lasting quality: Several weeks.

REPRODUCTIVE ORGANS

Stamens:

*Anthers.*—0.2–0.4 cm long.

*Filaments.*—Length: 0.2–0.4 cm. Color: 156B.

*Pollen.*—156C.

Pistils:

*Number.*—7.

*Length.*—0.2 cm.

*Stigma.*—157B.

*Style.*—1 cm long; 157B.

Fruit/seed: Not self-fertilizing.

GENERAL CHARACTERISTICS

1. Suitable as a potting plant and as a bedding plant.
2. Possible as a cut flower.
3. Long-lasting.
4. Not susceptible to flower shattering.
5. Growth regulators not required.
6. Branching is better after pinching.
7. Two-colored flower.
8. Very decorative.
9. Heat tolerant, less tolerant to drought and not hardy in winter.

I claim:

1. A new and distinct variety of angelonia plant substantially as shown and described.

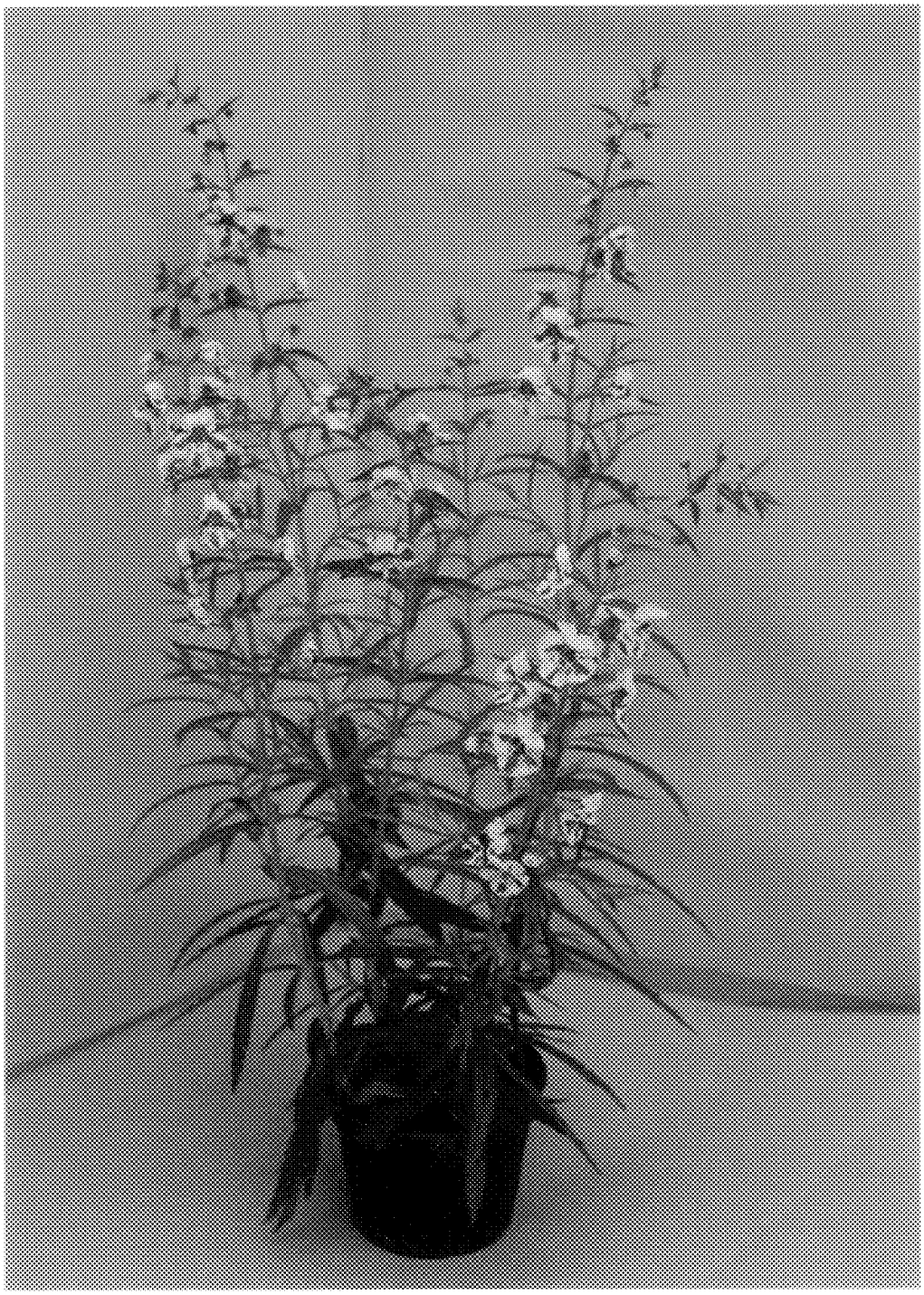

* * * * *